US006218357B1

(12) United States Patent
Terauchi

(10) Patent No.: US 6,218,357 B1
(45) Date of Patent: Apr. 17, 2001

(54) FIBROIN FLUID AND PROCESS FOR THE PRODUCTION THEREOF

(75) Inventor: Seiji Terauchi, Westkoganei 1-225, 2, Maehara-cho 4-chome, Koganei-shi, Tokyo (JP)

(73) Assignees: Seiji Terauchi, Tokyo (JP); Hiroshi Chinzai, Tokyo (JP)

( * ) Notice: Subject to any disclaimer, the term of this patent is extended or adjusted under 35 U.S.C. 154(b) by 0 days.

(21) Appl. No.: 08/909,068

(22) Filed: Aug. 14, 1997

(30) Foreign Application Priority Data

Aug. 15, 1996 (JP) ..................................................... 8-215541

(51) Int. Cl.⁷ ............................. A01N 37/18; A61K 38/39
(52) U.S. Cl. .................. 514/2; 514/21; 514/802; 514/824; 514/844; 530/350
(58) Field of Search ..................................... 424/400, 520, 424/538; 514/2, 12, 21, 802, 824, 844, 845, 846, 847, 848, 873; 530/350

(56) References Cited

U.S. PATENT DOCUMENTS 4,233,211 * 11/1980 Ohtomo et al. ....................... 530/353
4,233,212 * 11/1980 Otoi et al. ............................. 530/353

FOREIGN PATENT DOCUMENTS 61-276825 * 12/1986 (JP) .
08268905 * 10/1996 (JP) .

* cited by examiner

*Primary Examiner*—Nancy Degen
(74) *Attorney, Agent, or Firm*—Wenderoth, Lind & Ponack, L.L.P.

(57) ABSTRACT

A fibroin fluid obtained by adding carbon dioxide to a fibroin aqueous solution and then completely removing the carbon dioxide by pressure reduction or heating has fibroin microstructures which are dispersed in a dispersing medium, the fibroin fluid, unlike a conventional fibroin gel, having a fluidity sufficient for bringing it into the sate of a cream, having the property of excellent humidity retention and being widely usable as an agent for decreasing cholesterol or cosmetic.

20 Claims, 3 Drawing Sheets

FIBROIN FLUID AND PROCESS FOR THE PRODUCTION THEREOF

BACKGROUND OF THE INVENTION

1. Field of the Invention

The present invention relates to a fibroin fluid for use as a main ingredient or an additive in the fields of pharmaceuticals, cosmetics, hygiene or foods.

2. Description of the Related Art

As far as fibroin is concerned, a fibroin in a gel state is known. The fibroin in a gel state is obtained by adding an acid such as citric acid or acetic acid to silk protein to decrease its pH to an isoelectric point, or by adding sericin or other polysaccharide as a gelating agent.

A fibroin in a gel state ("fibroin gel" hereinafter) has a network structure in its entire system so that it is of one mass as a whole gel, and as a result, it cannot be brought into a "cream" state. Further, the fibroin gel is poor in water retention, and when the gel is allowed to stand, it cracks since contained water is lost.

On the other hand, when a fibroin gel is prepared by adding an additive such as citric acid or the like, it is difficult to remove the additive after the gelation, and the residual additive as an impurity in the gel has an adverse effect on the quality of an end product obtained from the fibroin gel. Moreover, the added gelating agent such as citric acid or other acids is not only present as an impurity, but it works on the crosslinked structure of fibroin to prevent the fibroin gel from exhibiting the adsorption capacity inherent to the fibroin gel.

As described above, fibroin gel has physical problems that it cannot be brought into a cream state and is poor in water retention, and it also has a production-wise problem that it contains an additive which causes a poor product quality. Therefore, although fibroin itself has a potential for its wide applications in the fields of pharmaceuticals, foods and cosmetics, these applications of the fibroin gel are impossible, and the use of fibroin is limited to very narrow fields.

SUMMARY OF THE INVENTION

The present invention has been made in view of the above problems, and the object thereof is to make it possible to apply fibroin widely to the fields of pharmaceuticals, foods and cosmetics.

The present invention relates to a fibroin fluid having a fluidity sufficient for bringing it into a cream state, unlike a conventional fibroin having only a jelly-like fluidity.

The present inventor has completed the present invention by finding the following. That is, a fibroin fluid obtained by a method in which carbon dioxide is added to a fibroin aqueous solution and the carbon dioxide is completely removed by pressure reduction or heating, has fibroin microstructures which are dispersed in a dispersing medium. Differing from a conventional fibroin gel, the above fibroin fluid has a fluidity sufficient for bringing it into the physical state of a cream, has the property of excellent humidity retention over a conventional fibroin gel and has wide usefulness as an agent for decreasing cholesterol or a cosmetic.

Unlike a homogeneous product such as a fibroin aqueous solution in which fibroin is dissolved in water, the fibroin fluid of the present invention is a mixture in which solid fibroin microstructures having a size of about 100 $\mu$m are dispersed in a dispersing medium.

Each of the fibroin microstructures constituting the fibroin fluid is a porous filmy substance having a steric branching structure. The fibroin microstructures of the fibroin fluid produced by the process of the present invention have a size of about 100 $\mu$m, and the distribution of sizes of the fibroin microstructures is not very broad.

Further, the dispersing medium in which the fibroin microstructures are dispersed is typically water, while the dispersing medium may be selected from media similar to water, such as lower alcohols. However, an organic solvent which may alter the fibroin itself cannot be used.

In the fibroin fluid of the present invention, fibroin microstructures which are of porous filmy substances having a steric branching structure present in a dispersed state. The fibroin fluid which is a mixture of units of the above fibroin microstructures, provided by the present invention, has a greater fluidity, and has excellent water retention as compared to a conventional fibroin gel.

The fibroin fluid of the present invention does not contain any of citric acid, polysaccharides or other gelating agent which inevitably remains in a conventional fibroin gel. The fibroin fluid of the present invention is therefore free of any adverse effects which these impurities have, and it can be used in the fields of pharmaceuticals, cosmetics, foods and other industrial products.

The fibroin fluid of the present invention can be easily and inexpensively produced by a method in which carbon dioxide is added to a fibroin solution to form a fluid and then the carbon dioxide is completely removed from the fluid by pressure reduction or heating. According to the process for the production of a fibroin fluid, provided by the present invention, the carbon dioxide added for forming a fibroin fluid can be completely removed in a short period of time by heat treatment or pressure-reduction treatment.

More specifically, first, carbon dioxide is mixed with a fibroin solution to adjust the pH of the solution close to a fibroin isoelectric point, whereby a fibroin fluid formed of units of fibroin microstructures is obtained. Then, the added carbon dioxide is removed from the system (fibroin fluid) by pressure reduction or heating. In this case, the carbon dioxide is completely removed from the system in a short period of time regardless of the structure of the fibroin microstructures. According to the above production process, therefore, a pure fibroin fluid can be easily obtained.

The fibroin aqueous solution can be obtained by a well known method. In the present invention, the fibroin aqueous solution is prepared by dissolving fibroin in a calcium chloride aqueous solution and then removing the calcium chloride from the aqueous solution by dialysis, the fibroin aqueous solution may be prepared by a method in which fibroin is dissolved in a copper-ethylenediamine complex salt solution, the resultant solution is neutralized with acetic acid and dialyzing the neutralized solution with flowing water, or by a method in which fibroin is dissolved in a lithium bromide aqueous solution or a calcium nitrate aqueous solution and then removing the lithium bromide or calcium nitrate by dialysis.

Further, the fibroin for preparing the fibroin aqueous solution is obtained by removing sericin from silkworm pod or silk yarn. The sericin can be removed from silkworm pod or silk yarn by a known method, for example, in which the silkworm pod or silk yarn is treated with hot water or a diluted alkali. For completely removing the sericin, it is preferred to use an alkali.

When carbon dioxide is dissolved in the fibroin aqueous solution, not much change takes place at the time the solution is formed. However, when the solution is allowed to stand for a while, the solution changes to a suspension to form a fibroin fluid. In general, the standing period of time is approximately 10 days to 2 weeks, while it is sometimes outside the above period. When the fibroin aqueous solution has a high concentration, the fibroin aqueous solution is brought into the state of a white cream. When it has a low concentration, a supernatant is formed in an upper portion. When a supernatant is formed since the fibroin aqueous solution has a low concentration, a precipitate portion itself is a fibroin fluid. When the precipitate portion is recovered by filtration, the obtained fibroin fluid has a water content of about 98% and can be directly used as a material for forming a product.

In the fibroin fluid obtained by the above production process, filmy fibroin microstructures having a size of about 100 $\mu$m and having steric branching structures are uniformly dispersed without crosslinking one another.

Each of the fibroin microstructures which are uniformly dispersed contains a large amount of water. The amount of water contained in the fibroin microstructures is adjusted, whereby there can be obtained a fibroin fluid which is in the state of an easily spreadable cream, an emulsion or any other fluid. The fibroin microstructures which are units of the fibroin fluid can stand heating and pressure, and the structure of the fibroin microstructures is not broken by heat treatment or treatment with elevated pressure in the steps of sterilizing, molding, packaging, etc., for preparing products of pharmaceuticals, foods or cosmetics. It is therefore easy to handle the fibroin fluid.

The fibroin microstructures not only have steric branching structures, but also each of them has a number of fine pores. Due to the presence of a number of fine pores, the fibroin microstructures have a remarkably increased effect of adsorbing other substances. Furthermore, since the fibroin itself has both a hydrophilic portion and a hydrophobic portion, it can therefore adsorb any oil or alcohol regardless of their kinds.

The fibroin fluid of the present invention, which is a mixture of the above fibroin microstructures, has excellent activities for affinity with water, an oil or an alcohol, humidity retention and substance adsorption over a conventional fibroin in a gel state. Further, since the fibroin fluid of the present invention contains no impurities such as a gelating agent, etc., the fibroin microstructures have an advantageous effect of being capable of adsorbing other substance without any prevention by these impurities.

When the fibroin fluid of the present invention is prepared in a cholesterol-adsorbing form which can be administered into an organism by utilizing the activity of the fibroin microstructures for substance adsorption, it can be used as an agent for reducing cholesterol in blood. Further, the fibroin fluid of the present invention can be brought into the state of any one of a cream and an emulsion and has the activity for humidity retention, and in addition to these, the fibroin itself, which is a component of the fibroin fluid, has ultraviolet light absorption activity. It can be therefore used as/in a cosmetic. Containing no impurities, the fibroin fluid of the present invention can be used as a main ingredient or as an additive for a cosmetic.

The agent for decreasing cholesterol in blood can be orally administered for the therapeutical treatment and prevention of chlesterolosis, arterial sclerosis or cerebral infarction.

DESCRIPTION OF THE PREFERRED EMBODIMENTS

Figure 1:
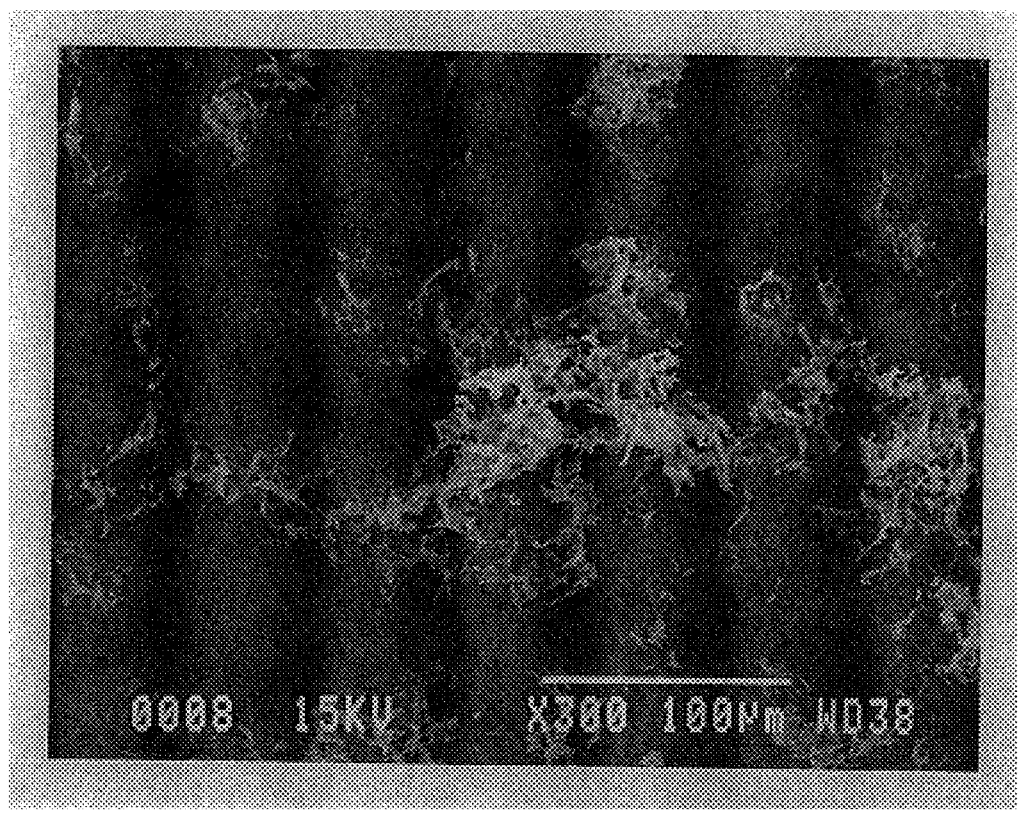
FIG. 1 is an electron microscopic photograph of a fibroin fluid of the present invention, taken at a magnification of 300 diameters.
Figure 2:
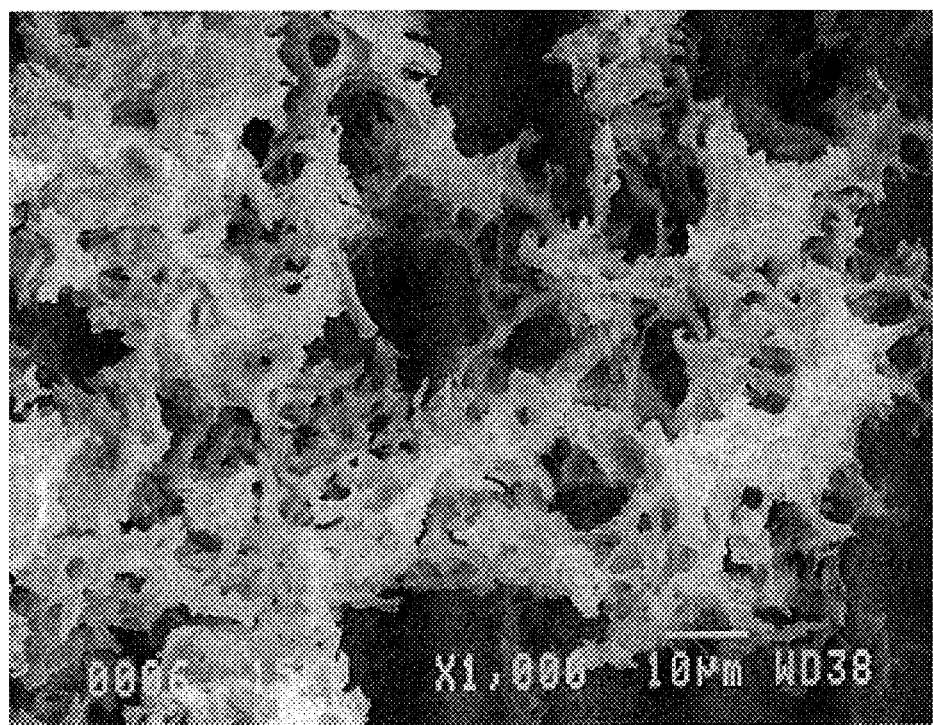
FIG. 2 is an electron microscopic photograph of a freeze-dried fibroin fluid of the present invention, taken at a magnification of 1,000 diameters.
Figure 3:
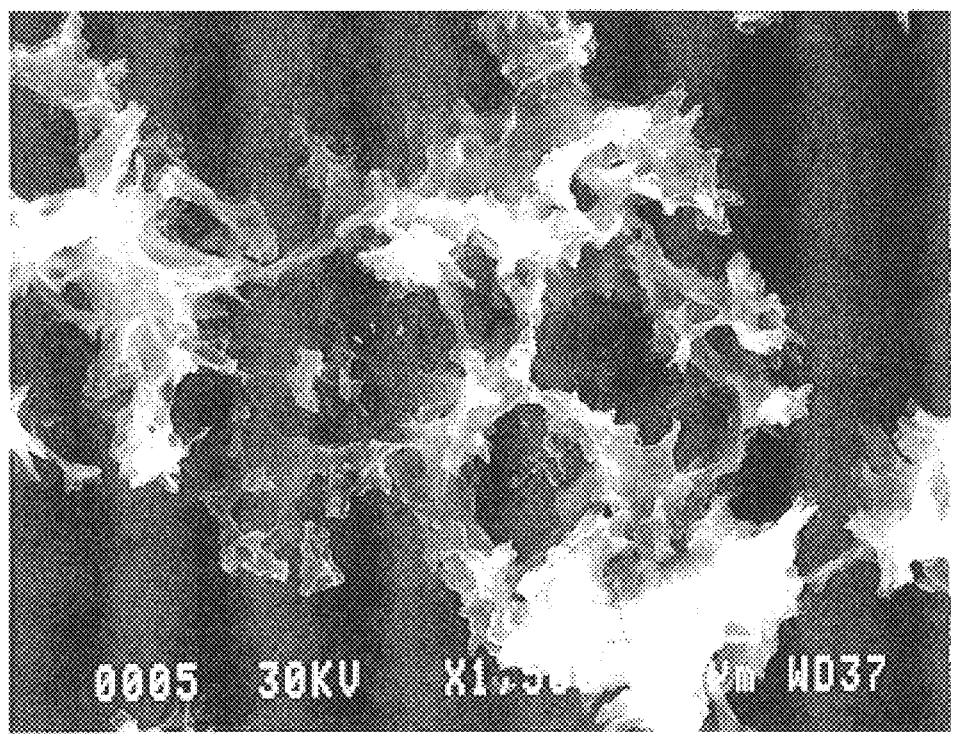
FIG. 3 is an electron microscopic photograph of a freeze-dried fibroin fluid of the present invention, taken at a magnification of 1,500 diameters.

In the fibroin fluid of the present invention, fibroin microstructures which are present independently of one another are uniformly dispersed as shown in the electron microscopic photographs of FIGS. 1 and 2. Each fibroin microstructure has a size of about 100 $\mu$m, and a number of fine pores are present as shown in FIG. 3.

One example of the process for the production of the fibroin fluid of the present invention will be explained below.

First, silkworm pods are, or silk is, boiled in a 0.5% sodium carbonate aqueous solution for 30 minutes to remove sericin, and then dissolved in a 50% calcium chloride aqueous solution. Then, the resultant solution is dialyzed to remove calcium chloride, whereby a silk fibroin solution is obtained. The silk fibroin solution is mixed with carbon dioxide generally in an amount approximately twice, preferably approximately four times as large as the amount of the silk fibroin solution, to acidify the silk fibroin solution (pH 3–5), whereby a fluid is formed. When the fibroin concentration is high, there is obtained a fluid having a high viscosity in the state of a cream. When the fibroin concentration is low, there is obtained a fibroin fluid having a low viscosity. The viscosity or hardness of the above fibroin fluid can be adjusted as required by removing water by filtration.

After the fluid is formed, the carbon dioxide mixed with the silk fibroin can be completely removed by a single step of pressure-reduction or heating treatment. The fibroin microstructures in the fibroin fluid of the present invention are stable under high heat and high pressure, and suffer no influence in the sterilization treatment which is generally carried out, for example, under heat at 100° C. for 30 minutes for sterilization.

EXAMPLES

For explaining the properties of the fibroin fluid of the present invention, experiments and comparative experiments were conducted with regard to a fluid strength, the activity of humidity retention, the activity to adsorb cholesterol in blood and the activity to decrease LDL cholesterol and fats (lipids) in liver. These experiments and the experimental method will be explained below.

In Experiments 1 and 2, fibroin fluids obtained by the following method were used. That is, 20 g of silk was dissolved in a boiling solution of 500 g of calcium chloride in 500 ml of water, and then, impurities were removed by filtration. The obtained solution was dialyzed to remove the calcium chloride. Carbon dioxide was dissolved in the resultant solution to form a fluid, whereby a precipitate of fibroin microstructures was obtained. The carbon dioxide was removed by pressure-reduction, and the fluid was filtered to adjust the water content of the fluid, whereby a fibroin fluid having a volume of 900 cm$^3$ in the state of a cream was obtained (fibroin content 2.2%).

Experiment 1 (Comparative test on gel strength)

The fibroin fluid obtained in the same manner as in the above method and a conventional fibroin gel obtained by gelation with citric acid or acetic acid were compared with regard to gel strength. Both of these samples had a silk fibroin concentration of 2.0%. A cylinder having a diameter of 8 mm was pressed into the fluid or the gel, and each was measured for a resistance (g/cm$^2$) formed on a contact surface (Method of Hirabayashi, et al, (SEN-I GAKKAISHI VOL. 46, 521)). The above experiment was repeated five times. Table 1 shows the measurement results as an average value ± a standard error.

TABLE 1

Results of comparative test on gel strength

|  | Fibroin fluid of the present invention | Fibroin gel obtained by gelation with citric acid | Fibroin gel obtained by gelation with acetic acid |
|---|---|---|---|
| Gelation Strength (g/cm$^2$) | 63.4 ± 2.7 | 111.6 ± 4.9 | 124.8 ± 2.1 |

As shown in Table 1, the fibroin fluid of the present invention shows a remarkably low gel strength as compared with the conventional gels. The gel strength shows the network structure of the entire system of a gel. The above results therefore show that the structure of the fibroin gel (fluid) of the present invention completely differs from those of conventional gels. That is, it is because the fibroin fluid of the present invention is in a state where hydrous fibroin microstructures are dispersed therein and because it does not have any typical gel structure as a whole having a network structure as a mass that the fibroin fluid of the present invention shows the above decreased gel strength. Having the above state, there can be obtained a fluid in the state of a smooth cream.

Experiment 2 (Comparative test on humidity rentention capacity)

The fibroin fluids (water content 98%, 97%) obtained in the same manner as in the above method, fibroin gels (water content 98%, 97%) prepared by gelation with citric acid and gelatin gels (water content 98%, 97%) derived from collagen were compared. The gelatin gels derived from collagen were used for comparison, because it is known that gelatin gel has high humidity retention capacity and is widely used as a humidity retaining agent in cosmetics.

The above samples in an amount of 1,000 mg each were placed on plates, and the plates with the samples thereon were allowed to stand in a desiccator having a temperature of 25° C. and a relative humidity of 50% for 72 hours. Then, each sample was measured for a weight (mg) The above experiment was repeated three times.

Table 2 shows the measurement results as an average value ± a standard error.

TABLE 2

Results of comparative test on humidity retention activity

|  | Fibroin fluid of the present invention | Fibroin gel obtained by gelation with citric acid | Gelatin gel |
|---|---|---|---|
| Water content (98%) | 914 ± 4 mg | 842 ± 17 mg | 830 ± 13 mg |
| Water content (97%) | 944 ± 7 mg | 850 ± 10 mg | 885 ± 8 mg |

As shown in Table 2, the fibroin fluid of the present invention, which is formed of fibroin microstructures, shows excellent water retention capacity over collagen and the conventional fibroin gel.

It is known that conventional fibroin gel is porous and has the property of water retention, while the fibroin fluid of the present invention shows the property of much higher water retention. The reason therefore is as follows. The porous fibroin microstructures constituting the fibroin fluid of the present invention have filmy steric branching structures, and they have a number of fine pores thereby to increase adsorption areas. Moreover, presumably, the fibroin microstructures can be dispersed in a state in which they contain water.

In Experiment 3, a fibroin powder obtained by the following method was tested for the activity to decrease cholesterol in blood and to decrease lipids in liver. 60 g of silk was dissolved in a boiling solution of 500 g of calcium chloride in 500 ml of water, and then, impurities were removed by filtration. The obtained solution was dialyzed to remove the calcium chloride. Carbon dioxide was dissolved in the resultant solution to form a fluid, and the carbon dioxide was removed by pressure reduction. The resultant fluid was frozen with liquid nitrogen, and free-dried to give a fibroin powder.

Experiment 3 (Activity to decrease LDL-cholesterol and lipids in liver)

Each of a test plot and a control plot used eight rats having a high cholesterol (total cholesterol 185 ml/dl) in blood, which were fed with a nutrition-evaluating feed (AIN76, supplied by Tokyo Jikken Dobutsu K.K.) containing 1% of cholesterol for 7 days.

The rats in the control plot were fed with AIN76 feed for 7 days, and the rats in the test plot was fed with a feed (prepared by replacing 3% of cellulose of AIN76 feed with the above silk fibroin powder) for 7 days. Then, blood was taken from the heart of each rat, and the blood from each rat was measured for a total cholesterol amount, an HDL-cholesterol amount and an LDL-cholesterol amount. Further, the lipids in liver were evaluated by observing a liver tissue through a microscope and analyzing the weight of lipids (Folch method). The results were statistically handled, and Tables 3 and 4 show the results as an average value ± a standard error.

TABLE 3

Results of test for cholesterol in rat blood

|  | Cholesterol in rat blood (mg/dl) | |
|---|---|---|
| Items for measurement | Control plot | Test plot |
| Total cholesterol | 139 ± 5 | 102 ± 6 |
| HDL-cholesterol | 43 ± 4 | 42 ± 3 |
| LDL-cholesterol | 96 ± 7 | 60 ± 5 |

TABLE 4

Results of test for lipids in liver

|  | Lipid weight (mg/tissue) | |
|---|---|---|
| Item for measurement | Control plot | Test plot |
| Lipids in liver | 145 ± 4 | 110 ± 6 |

The above Tables 3 and 4 show that the fibroin powder of the present invention not only decreases arterial sclerosis-inducing LDL cholesterol in blood, but also decreases the lipids in liver, when orally administered.

Further, the microscopic observation of the liver tissues showed that the amount of fat globules in cells were remarkably decreased.

Experiment 4 (Test for the capability of adsorbing cholesterol)

The same fibroin powder as that used in Experiment 3 was tested for the capability of adsorbing cholesterol in a test tube. As a sample in a control test, a soybean protein decomposition product, which is considered to have the activity to decrease cholesterol, was used.

The fibroin powder or the soybean protein decomposition product in an amount of 40 mg was placed in a test tube, and 1 ml of 0.1 M bile salt (taurocholic acid, glycocholic acid) was added. The mixture was shaken for 2 hours and then ultrafiltrated, and the powder or the decomposition product was measured for an amount (mg/dl) of an adsorbed bile acid. Table 5 shows results.

TABLE 5

Test on the cholesterol-adsorbing capability

| Sample | Taurochloic acid | Glycocholic acid |
|---|---|---|
| Fibroin powder of the invention | 55 ± 4 mg/dl | 42 ± 3 mg/dl |
| Soybean protein decomposition product | 44 ± 5 mg/dl | 33 ± 7 mg/dl |

As shown in Table 5, the fibroin powder of the present invention shows a high cholesterol absorbing capability. The above results show that the fibroin powder of the present invention easily bond to lipidic substances.

The results of Experiments 3 and 4 show that the fibroin microstructures constituting the fibroin powder or the fibroin fluid not only directly adsorb cholesterol but also adsorb cholesterol in blood in an organism when orally administered.

Test on toxicity

The fibroin fluid of the present invention is a protein which does not contain any impurities including an acid, and it is therefore safe to organisms. Further, if it is taken into consideration that silk pots are edible, or used as a food, in a certain part of Japan, it is clear that the fibroin fluid of the present invention can be used as an agent for decreasing cholesterol in blood, which agent can be orally ingested on a daily basis. For confirming the safety of a cholesterol-decreasing agent composed of the fibroin fluid of the present invention, the following toxicity test using rats was conducted.

Wister rats of age of 7 weeks were preliminarily fed with a nutrition-evaluating feed (AIN76, supplied by Tokyo Jikken Dobutsu K.K.) for 4 days. After the preliminary feeding, as a test plot, 10 rats were fed with a feed prepared by replacing 5% of sucrose of AIN76 feed with the fibroin powder, for 3 weeks. Separately, as a control plot, 10 rats were fed with AIN76 for 3 weeks. The rats in the test plot and the rats in the control plot were compared. The results of the acute toxicity test were as shown below.

(1) $LD_{50}$ value: at least 3,400 mg

The $LD_{50}$ value is described as such, while the fibroin fluid itself had no toxicity, and no rat died during the test.

(2) After the test, the rats were sacrificed, measured for weights of bodies and organs, and were anatomically studied. Table 6 shows the ratios (%) of the weights of organs to the weights of the bodies.

TABLE 6

Influence of fibroin fluid on organs when it was orally ingested

| | Test plot | Control plot |
|---|---|---|
| Liver | 5.29 ± 0.15 | 5.33 ± 0.16 |
| Kidney | 0.81 ± 0.11 | 0.82 ± 0.12 |
| Pancreas | 0.21 ± 0.01 | 0.21 ± 0.02 |
| Stomach | 0.33 ± 0.02 | 0.32 ± 0.03 |
| Small intestine | 1.79 ± 0.09 | 1.77 ± 0.12 |
| Spermary | 0.82 ± 0.03 | 0.82 ± 0.03 |

After the test, there was found no statistically significant difference in the weight ratios of liver, kidney, pancreas, stomach, small intestine and spermary to the body between the test plot and the control plot. Further, when the organs were anatomically studied, there was found no difference between the test plot and the control plot.

Experiment 5 Test on capability of absorbing ultraviolet light

The fibroin fluid in a cream state according to the present invention, which was the same as that used in Experiment 2, and a fibroin gel obtained by gelation with citric acid were compared. The fibroin gel obtained by gelation with citric acid was immersed in water for 24 hours for minimizing the influence of the remaining acid.

0.5 Gram of the above fibroin fluid in the state of a cream was applied to right arms of the two normal people in the brachium in an area of 3 $cm^2$. While the above applied area each was covered with a black paper sheet having a circular hole having a diameter of 1 cm, the applied area was exposed to ultraviolet light from an ultraviolet light sterilization lamp (National 15 W) at a distance of 30 cm for 10 minutes. Further, an area to which the fibroin gel obtained by gelation with citric acid and an area to which the fibroin fluid was not applied were exposed in the same manner.

The results of the above test were as follows. When the fibroin fluid was not applied, and when the fibroin gel obtained by gelation with citric acid was applied, a red spot occurred on the skin. When the fibroin fluid was applied, no change was found on the skin. These results show that the fibroin fluid has the capability of absorbing ultraviolet light.

Production Process

The process for the proudction of the fibroin fluid formed of fibroin microstructures, provided by the present invention, will be explained with reference to Examples hereinafter.

Example 1

20 Grams of silk was dissolved in a boiling solution of 500 g of calcium chloride in 500 ml of water, and the mixture was filtered to remove impurities. The filtrate was dialyzed to remove the calcium chloride. Carbon dioxide was dissolved in the resultant solution to obtain a precipitate of fibroin microstructures. In this Example, solid carbon dioxide (dry ice) was used as carbon dioxide, and dissolved as follows. The carbon dioxide was poured into the fibroin aqueous solution, and a container with the solution in it was plugged to dissolve the carbon dioxide. The carbon dioxide was removed by pressure reduction, and the water content of the fluid was adjusted by filtration to give the fluid having a size of 900 $cm^3$, whereby there was obtained a fibroin fluid (fibroin content 2.2%) in the state of a cream, which was formed of units of fibroin microstructures.

Example 2

30 Grams of silk was dissolved in a boiling solution of 500 g of calcium chloride in 500 ml of water, and the mixture was filtered to remove impurities. The calcium chloride was removed by dialysis to obtain 1,000 ml of a fibroin solution. Carbon dioxide was dissolved in the fibroin solution to obtain a precipitate of fibroin microstructures. In this Example, solid carbon dioxide (dry ice) was used as carbon dioxide, and dissolved as follows. The carbon dioxide was poured into the fibroin aqueous solution, and a container with the solution in it was plugged to dissolve the carbon dioxide. The carbon dioxide was removed by pressure reduction, and the water content of the fluid was adjusted by filtration to give 1,000 $cm^3$ of a fibroin fluid formed of units of fibroin microstructures.

Example 3

60 Grams of silk was dissolved in a boiling solution of 500 g of calcium chloride in 500 ml of water, and the mixture was filtered to remove impurities. The filtrate was dialyzed to remove the calcium chloride. Carbon dioxide was dissolved in the resultant solution to obtain a precipitate, and then, the carbon dioxide was removed by pressure reduction. In this Example, solid carbon dioxide (dry ice) was used as carbon dioxide, and dissolved as follows. The carbon dioxide was poured into the fibroin aqueous solution, and a container with the solution in it was plugged to dissolve the carbon dioxide. The resultant fluid was frozen with liquid nitrogen, and then freeze-dried to give a fibroin powder composed of fibroin microstructures.

The carbon dioxide used in Examples 1 to 3 may be liquefied carbon dioxide or a solid carbon dioxide such as dry ice.

Utility

The fibroin fluid of the present invention has fluidity sufficient for forming a fluid in the state of a cream, an emulsion or some other flowable substance, and exhibits affinity with an oil, water or an alcohol. At the same time, it does not at all contain any gelating agent such as citric acid, etc. Therefore, it can be widely used as a main ingredient or an additive in the fields of pharmaceuticals, cosmetics, hygiene and foods.

That is, a conventional fibroin gel has a bonded network structure as a whole, while the fibroin fluid of the present invention is formed of a number of fibroin microstructures which are independently dispersed. The fibroin fluid provided by the present invention is therefore novel and has wide application fields. The fibroin fluid which is stable in the state of a cream for a long period of time has utility particularly in the fields of pharmaceuticals, cosmetics and foods.

Further, each of the fibroin microstructures has a number of fine pores present, and, the fibroin fluid is excellent in the adsorption of other substances. Owing to this high adsorption capability, the fibroin fluid of the present invention has an effect of directly or indirectly (orally) decreasing arterial sclerosis-inducing LDL-cholesterol in blood and lipids in liver, and can be used as a cholesterol-decreasing agent safe to human bodies.

Further, the fibroin fluid of the present invention exhibits high affinity with water, an oil or an alcohol, and can be mixed with them in any ratio as required. It can have any form of a cream, an emulsion, jelly, or the like and it can be therefore processed in any form. It has the capacity of both water retention and ultraviolet light absorption, and it therefore has high use values in the fields of pharmaceuticals, foods and cosmetics.

As explained above, the fibroin fluid of the present invention is excellent in water retention, adsorption of substances, affinity with an oil or an alcohol, the capability of decreasing cholesterol and the capability of absorbing ultraviolet light, and according to the process of the present invention, the fibroin fluid can be mass-produced by a simple inexpensive method requiring not much labor, and the fibroin fluid can be provided for use as a main ingredient or an additive in the fields of pharmaceuticals, medical treatment, cosmetics, hygiene and foods.

What is claimed is:

1. A gelating agent-free fibroin fluid formed of a dispersion in which fibroin microstructures are dispersed in a dispersing medium.

2. The fibroin fluid according to claim 1, wherein the fibroin fluid is water-content-adjusted and in the physical state of a cream.

3. An agent which is humidity-retaining and has ultraviolet light properties containing an effective amount of the fibroin powder recited in claim 2.

4. A cosmetic containing the agent of claim 3.

5. A fibroin powder obtained by freeze-drying the fibroin fluid recited in claim 1.

6. An agent which is humidity-retaining and has ultraviolet-absorbing properties containing an effective amount of the fibroin powder recited in claim 3.

7. An agent for decreasing cholesterol in blood, which contains an effective amount of the fibroin fluid recited in claim 5.

8. A method of therapeutical treatment of cholesterolosis, arterial sclerosis or cerebral infarction, which comprises orally administering the agent for decreasing cholesterol in blood recited in claim 7.

9. An agent which is humidity-retaining and has ultraviolet-absorbing properties containing an effective amount of the fibroin fluid recited in claim 1.

10. An agent for decreasing cholesterol in blood, which contains an effective amount of the fibroin fluid recited in claim 1.

11. A gelating agent-free fibroin fluid, obtained by dissolving carbon dioxide in a fibroin aqueous solution to acidify the fibroin aqueous solution, thereby obtaining a fluid and then removing the carbon dioxide from the fluid.

12. A fibroin powder obtained by freeze-drying the fibroin fluid recited in claim 11.

13. A process for producing a fibroin fluid, which comprises dissolving carbon dioxide in a fibroin aqueous solution to acidify the fibroin aqueous solution and removing the carbon dioxide from the acidified fibroin aqueous solution resulting in a fibroin fluid.

14. The process according to claim 13, wherein the fibroin aqueous solution is obtained by removing sericin from silkworm pod or silk yarn, then dissolving the silkworm pod or silk yarn in a calcium chloride aqueous solution and removing the calcium chloride by dialysis.

15. The process according to claim 13, wherein the carbon dioxide in an amount at least twice as large as the amount of the fibroin aqueous solution is mixed with the fibroin aqueous solution.

16. The process according to claim 13, wherein the carbon dioxide in an amount approximately 4 times as large as the amount of the fibroin aqueous solution is mixed with the fibroin aqueous solution.

17. The process according to claim 13, wherein the carbon dioxide in the form of a gas is dissolved in the fibroin aqueous solution or the carbon dioxide in the form of a solid is dissolved in the fibroin aqueous solution.

18. The process according to claim 13, wherein the carbon dioxide is mixed with the fibroin aqueous solution to obtain a mixture having a pH of or around an isoelectric point of fibroin.

19. The process according to claim 18, wherein the carbon dioxide is mixed with the fibroin aqueous solution to form a mixture having a pH of 3 to 4.

20. The process according to claim 13, wherein the carbon dioxide is removed by pressure reduction or heat treatment of the fibroin aqueous solution in which the carbon dioxide is dissolved.

* * * * *